United States Patent [19]

Wu et al.

[11] Patent Number: 5,739,321
[45] Date of Patent: Apr. 14, 1998

[54] 3-HYDROXY γ-LACTONE BASED ENANTIONSELECTIVE SYNTHESIS OF AZETIDINONES

[75] Inventors: Guang-Zhong Wu, Somerville; Xing Chen, Plainsboro; Yee-Shing Wong, Florham Park; Doris P. Schumacher, Bedminster; Martin Steinman, Livingston, all of N.J.

[73] Assignee: Schering Corporation, Kenilworth, N.J.

[21] Appl. No.: 655,785

[22] Filed: May 31, 1996

[51] Int. Cl.⁶ .................................. C07D 205/04
[52] U.S. Cl. ........................... 540/200; 540/362
[58] Field of Search ........................... 540/200, 362

[56] References Cited

FOREIGN PATENT DOCUMENTS

95/08532  3/1995  WIPO .
97/16424  5/1997  WIPO .

OTHER PUBLICATIONS

Panfil et al, *Tetrahedron*, vol. 47, No. 48 (1991), pp. 10087–10094.

Panfil et al, *Chemical Abstracts*, vol. 109, 38139j, 1988.

*Primary Examiner*—Joseph McKane
*Attorney, Agent, or Firm*—Anita W. Magatti

[57] ABSTRACT

The invention relates to a process for producing the compound of the formula

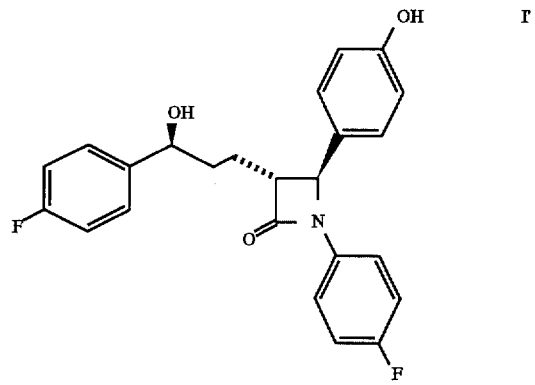

which comprises reacting lactone of formula II

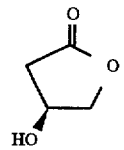

with an imine of formula III':

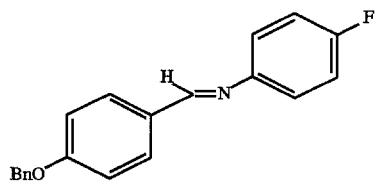

and converting the resulting chiral diol of formula VI:

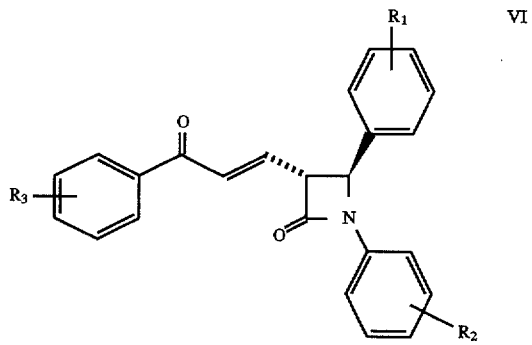

through several steps to obtain a compound of formula I'.

2 Claims, No Drawings

3-HYDROXY γ-LACTONE BASED ENANTIOSELECTIVE SYNTHESIS OF AZETIDINONES

SUMMARY OF THE INVENTION

This invention provides an improved process for producing azetidinones useful as hypocholesterolemic agents, as disclosed in co-owned, copending PCT International Application No. PCT/US92/05972. More particularly, this invention provides the steps of producing an azetidinone represented by the formula I.

SUMMARY OF THE INVENTION

This invention provides a process for producing a compound of the formula:

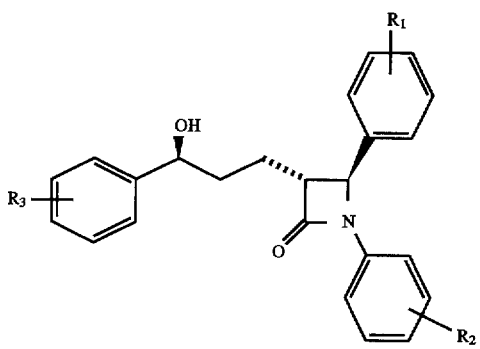

I wherein:

$R^1$, $R^2$ and $R^3$ are independently selected from the group consisting of:

(a) H;

(b) halo;

(c) —$OR^5$ wherein $R^5$ is selected from: H, $C_1$ to $C_6$ alkyl, aryl, aralkyl, heteroaryl, $C_2$ to $C_6$ alkenyl, $C_2$ to $C_6$ alkynyl, $C_3$ to $C_7$ cycloalkyl, $C_3$ to $C_7$ cycloalkenyl, or —$C(O)R^6$ (wherein $R^6$ is selected from $C_1$ to $C_6$ alkyl, aryl, or —$OR^7$ wherein $R^7$ is $C_1$ to $C_6$ alkyl or aryl); and (d) —$C(O)R^8$ wherein $R^8$ is selected from $C_1$ to $C_6$ alkyl, aryl, heteroaryl, aralkyl, cycloalkyl, —$OR^9$ (wherein $R^9$ is selected from $C_1$ to $C_6$ alkyl or aryl), and —$N(R^{10})_2$ (wherein each $R^{10}$ is independently selected from H, $C_1$ to $C_6$ alkyl and aryl);

$R^4$ is selected from H and —OH;

This process comprises reaction of a γ-lactone and an imine to form a β-lactam, followed by a chiral reduction.

DETAILED DESCRIPTION

As used herein, the term "lower alkyl" means straight or branched alkyl chains of 1 to 6 carbon atoms. Alternatively, the number of carbon atoms may be specified. Thus, "$C_1$ to $C_6$ alkyl" means straight or branched alkyl chains of 1 to 6 carbon atoms. "Lower alkoxy" refers to alkoxy groups having 1 to 6 carbon atoms. Alternatively, the number of carbon atoms may be specified. Thus, "$C_1$ to $C_6$ alkoxy" means straight or branched alkoxy chains of 1 to 6 carbon atoms.

"Alkenyl" means straight or branched carbon chains having one or more double bonds in the chain, conjugated or unconjugated, and alkadienyl refers to chains having two double bonds in the chain; Alternatively, the number of carbon atoms may be specified. Thus, "$C_1$ to $C_6$ alkenyl" means straight or branched alkenyl chains of 1 to 6 carbon atoms. "Alkynyl" means straight or branched carbon chains having one or more triple bonds in the chain. Alternatively, the number of carbon atoms may be specified. Thus, "$C_1$ to $C_6$ alkynyl" means straight or branched alkynyl chains of 1 to 6 carbon atoms.

Where an alkyl, alkenyl or alkynyl chain joins two other variables and is therefore bivalent, the terms alkylene, alkenylene and alkynylene are used.

"Aryl" (including substituted aryl) means a carbocyclic group containing from 6 to 15 carbon atoms and having at least one aromatic ring (e.g. aryl is a phenyl ring), with all available substitutable carbon atoms of the carbocyclic group being intended as possible points of attachment, said carbocyclic group being optionally substituted (e.g. 1 to 3) with one or more of halo, alkyl, hydroxy, phenoxy, $CF_3$, amino, alkylamino, dialkylamino, or —$NO_2$;

"Aralkyl" means an alkyl group as defined above, in which an aryl group as defined above is substituted for one of the alkyl H atoms, e.g., benzyl, 4-nitro-benzyl' 4-methoxy benzyl and 4-chlorobenzyl;

"Acid" means an organic acid such as p-toluene sulfonic acid, trifluoroacetic acid or trifluoromethane sulfonic acid. Alternatively "acid" means an inorganic acid such as sulfuric acid, hydrochloric acid, or phosphonic acid.

"Hydogenation catalyst" means a transition metal or its salt such as Pd/C, Pt/C, Raney nickel, Rh/C, Ru/C, PdO, PtO, or $(PPh_3)_3RhCl$.

"Cycloalkenyl" mean a cycloalkane of 4 to 10 carbon atoms with one or more double bonds in the ring.

"Bn" means benzyl. "BnO" means benzyloxy.

"Cycloalkyl" means a saturated carbon ring of 3 to 6 carbon atoms, while "cycloalkylene" refers to a corresponding bivalent ring, wherein the points of attachment to other groups include all positional isomers. Alternatively, the number of carbon atoms may be specified. Thus, "$C_3$ to $C_6$ cycloalkyl" means saturated carbon rings of 3 to 6 carbon atoms.

"Halogeno" or "hal" or "halogen" refers to fluorine, chlorine, bromine or iodine radicals.

"Heteroaryl" includes all positional isomers for a given heteroaryl group as defined herein, for example 2-pyridyl, 3-pyridyl and 4-pyridyl. Benzofused heteroaryl refers to radicals formed by the bonding of a benzene radical to adjacent carbon atoms on a heteroaryl ring; examples are indolyl, quinolyl, quinazolinyl, quinoxalinyl, benzotriazolyl, indazolyl, benzoxazolyl, benzothienyl and benzofuranyl.

"Ph" means phenyl.

"Suitable inert organic solvent" means any organic solvent or combination of solvents that is unreactive in the reaction being conducted and is a solvent for the reactants. Such solvents used in the various reactions of this invention are identified in the discussion of reaction schemes and in the examples. Typical suitable solvents are halogenated compounds such as chloroform or dichloromethane; heterocyclic compounds such as tetrahydrofuran (THF); 1,3-dimethyl-3,4,5,6-tetrahydro-2(1H)-pyrimidinone, dimethylformamide (DMF); dimethylsulfoxide (DMSO), lower alkanols ($C_1$–$C_6$ branched or straight chain alkanols) such as methanol; acetonitrile; and carbocyclic aromatics such as toluene.

"Lewis acid" means a Lewis acid such as $BF_3$.etherate or $TiCl_4$.

In one aspect, the process of this invention comprises reaction of a γ-lactam and an imine to form a β-lactam, followed by a chiral reduction according to Reaction Scheme A just below.

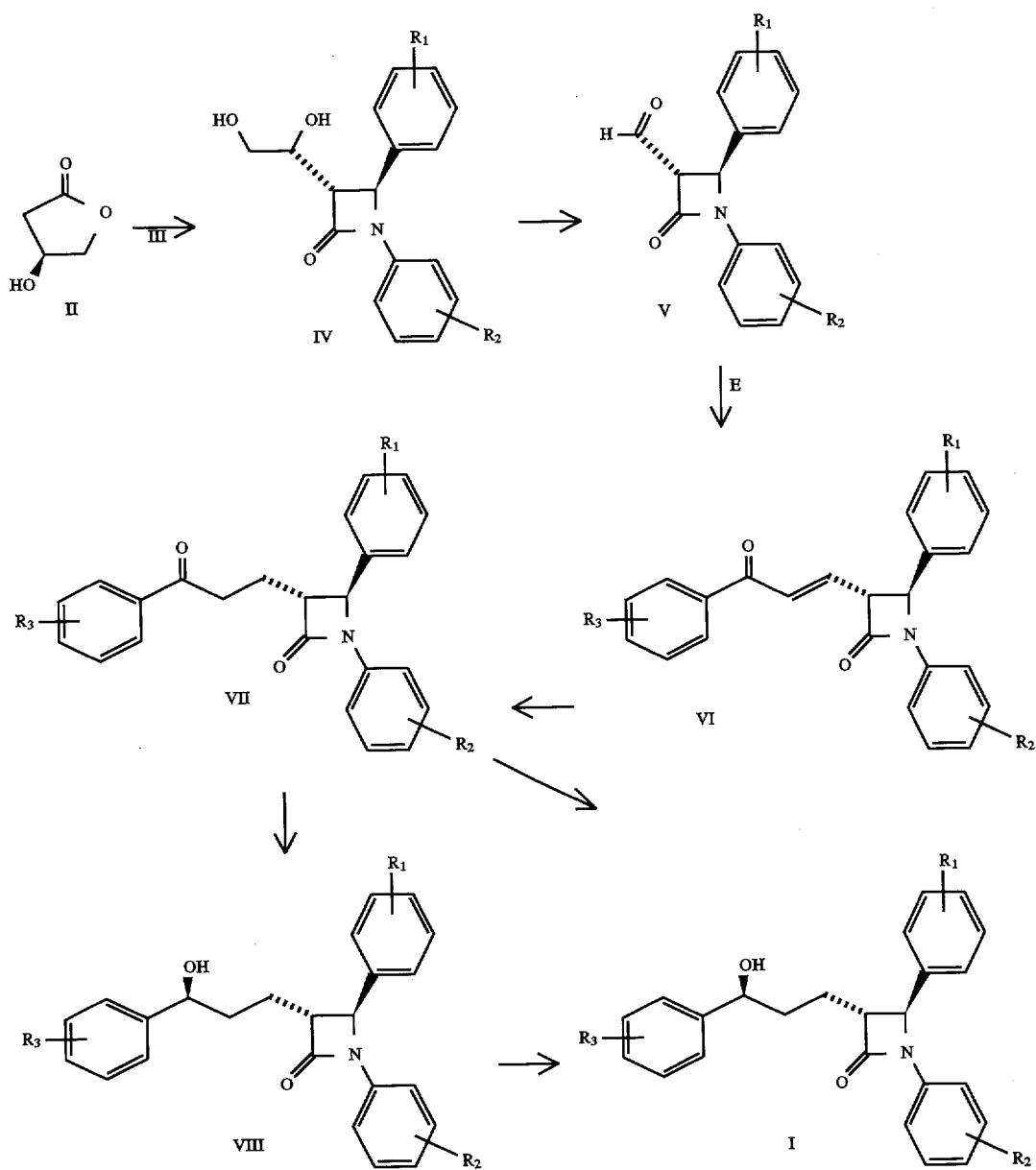
This process, designated Method A, for producing compounds of formula I, wherein the moieties
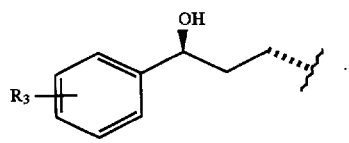
and
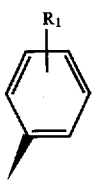
have trans relative stereochemistry, comprises the following steps:
(a) reacting lactone of formula II with an imine of formula III

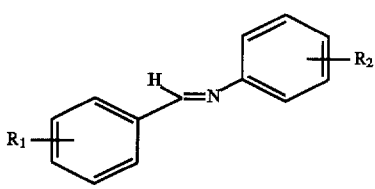

in the presence of a strong base to obtain a chiral diol of formula IV;

(b) oxidizing the resulting chiral diol of formula IV to the corresponding aldehyde of formula V with an oxidizing agent such as $NaIO_4$ or $H_5IO_6$;

(c) condensing the aldehyde of formula V with an enolether of the formula E followed by acid catalyzed dehydration.

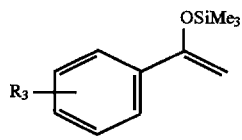

to obtain a compound of formula VI;

(d) hydrogenation of a compound of formula VI with a hydrogenation catalyst agent such as hydrogen over palladium or hydrogen and $(PPh_3)RhCl$ on carbon to form a compound of formula VII;

(e) conducting a chiral catalytic reduction of the compound of formula VII with a chiral catalyst such as

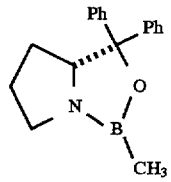

$BH_3(CH_3)_2S$ to obtain a compound of formula VIII;

(f) conducting a debenzylation reaction of a compound of formula VIII with a hydrogenating agent such as Pd/C/$NH_3HCO_2H$ to obtain a compound of formula I.

Method A as described in more detail is as follows. In Reaction Scheme A, the lactone II is treated in a strong base such as lithium diisopropylamide in the presence of an imine of formula III

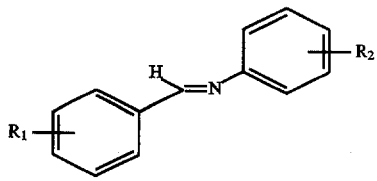

under a dry atmosphere, at a temperature in the range of about $-15°$ to about $-35°$ C. in a suitable inert organic solvent, e.g., 1,3-dimethyl-3,4,5,6-tetrahydro-pyrimidinone (DMPU), to produce a β-lactam of formula IV. The reaction can be quenched by an acid such as acetic acid, and a trans β-lactam of formula IV can be recovered by extraction followed by crystallization. Because trans β-lactam cyclizes faster than cis β-lactam, formation of a tans isomer is favored. This cyclization can be greatly accelerated by addition of additives such as LiCl or LiBr (in a solvent such as DMF) resulting in further selectivity of trans β-lactam formation. A crystallization step at this stage further improves the ratio of trans to cis β-lactam to 95:5. In this reaction, use of a weaker coordination metal favors the formation of a trans β-lactam of formula IV. Thus, in this reaction, the use, as a base of sodium —LiHMDA, favors the formation of a trans β-lactam of formula IV as opposed to the cis isomer, and is preferred as opposed to $Et_2Zn/LDA$ or $LiN(Pr-i)_2$. Also in this reaction, a lower temperature favors the formation of a trans β-lactam of formula IV, as opposed to the cis isomer; and thus $-35°$ C., is preferred over $-25°$ C. or $-15°$ C.

Then, a β-lactam of formula IV is oxidized by treatment with an oxidizing agent such as $NaIO_4$ in a mixture of solvents such as THF and water at a temperature between about $10°$ C. and $25°$ C., with about $10°$ C. to about $15°$ C., being preferred. The ratio of the oxidizing agent, $NaIO_4$, to diol is as follows: if the diol is present at 1.0 equivalent, then the $NaIO_4$ is present at 1.0–2.0 equivalents, with 1.5 equivalent being preferred. The organic solvent for the reaction is a polar aprotic solvent such as acetonitrile or THF. The reaction is quenched by adding the reaction mixture to ice water. The resulting aldehyde of formula V is extracted and concentrated for use in the next step of the process.

Then, an aldehyde of formula V is reacted with the enolether of the formula E:

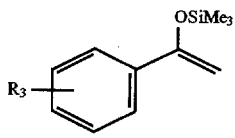

in an aprotic anhydrous organic solvent such as toluene in the presence of a Lewis acid such as $BF_3$.etherate at a temperature in the range of about $-78°$ C. to about $-20°$ C., with about $-40°$ C. to about $-20°$ C. being preferred. The resulting aldol reaction can be quenched for example with a mixture of $NaHCO_3$, t-BuOMe and hydrogen peroxide. In this reaction, the ratio of the β-lactam and the enolether can be as follows: if the β-lactam is present at 1.0 equivalent, then the enolether can be present at 0.9 to 1.2 equivalent with 1.0 equivalent being most preferred. The ratio of the β-lactam and $BF_3$.etherate can be as follows: if the β-lactam is present at 1.0 equivalent, then $BF_3$.etherate can be present at 1.0 to 1.5, equivalent with 1.0 to 1.2, equivalent being preferred. The resulting solution containing aldol product was extracted and concentrated for the dehydration step which involves treatment with molecular sieves and an organic acid such as p-toluene sulfonic acid monohydrate. If the aldol product is present at 1.0 equivalent, then the p-toluene sulfonic acid monohydrate can be present at 0.4 to 0.8 equivalent, with 0.5 to 0.6 equivalent being preferred. The solvents which may be employed in this reaction include toluene, t-butyl methyl ether, or benzene. The molecular sieves which are used in this reaction are 3 Å or 4 Å and are present in the reaction at 100% to 200% weight/weight as compared to the aldol compound. The reaction temperature is about $35°$ C. to about $100°$ C., with the range of about $45°$ C. to about $60°$ C. being preferred. The resulting compound of formula VI

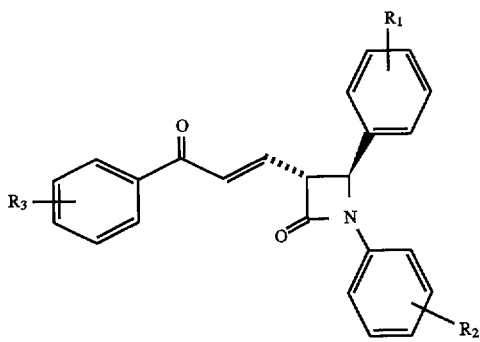

is filtered and concentrated for use in the next step of this process. (It will be appreciated that a compound of formula VI is formed with cis and trans stereochemistry. That is,

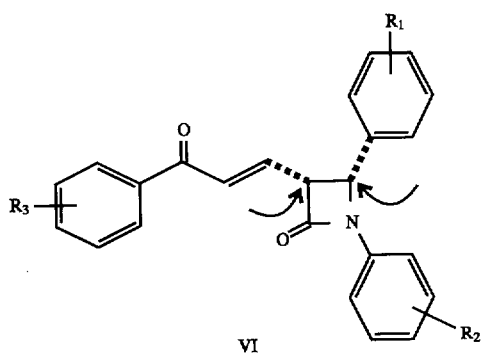

trans stereochemistry. That is,    cis    and

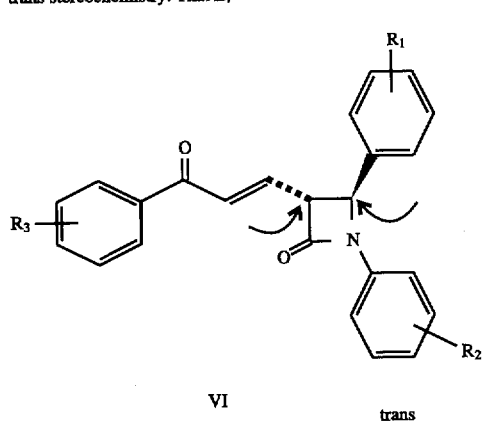

about the azetidinone ring as shown by the arrows in these diagrams. Obtention of the compound with the trans stereochemistry is necessary in order to get the desired final products of the invention.

In a preferred embodiment of the invention, an imine of the formula

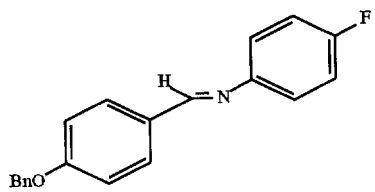

is used and an enolether of the formula

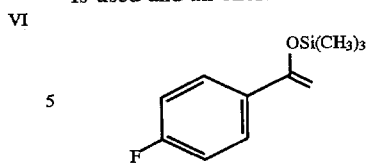

is used. Consequently the compound of formula VI which results has the structural formula VI':

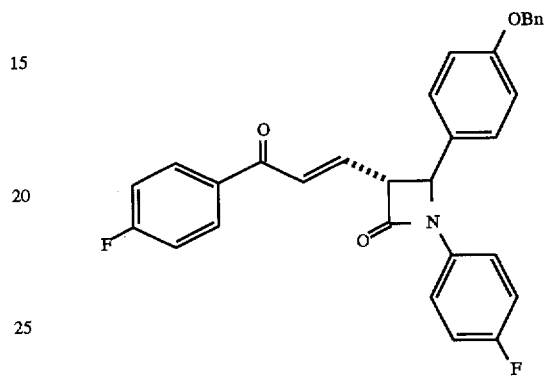

This resulting compound of formula VI is hydrogenated by treatment with a hydrogenating agent such as $(Ph_3P)_3RhCl/H_2$) under a hydrogen atmosphere in an organic solvent such as a mixture of ethyl acetate and methanol; methylene chloride; toluene; or benzene. The ratio of hydrogenating agent to the compound of formula VI is as follows: if the compound of formula VI is present at 1 mol %, then the hydrogenating agent is present at 0.1 to 10 mol %, with 0.3 mol % being preferred. The hydrogen atmosphere is present at 5 to 100 psi, with 40 to 60 psi being preferred. The reaction is run for 10 to 30 hours, with 14 to 16 hours being preferred. After extraction and concentration, the resulting compound of formula VII'

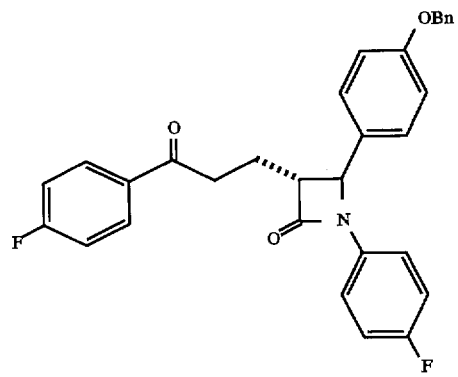

is used in the next step of the process.

The compound of formula VII' is chirally reduced by reaction in an anhydrous organic solvent such as $CH_2Cl_2$, tetrahydrofuran, or toluene, in the presence of a chiral reduction catalyst such as

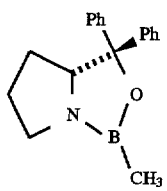

Compound of formula Q at a temperature in the range of about –30° to about 0° C., with a range of about –20° to about –10° C., being preferred. The reaction is run for about 1 to about 20 hours, with a range of about 3 to about 10 hours being preferred. The ratio of the compound of formula VII' to the compound of formula Q is as follows: if the compound of formula VII' is present in 1 mol % then the compound of formula Q is present in a range of about 5 mol % to 100 mol %, with 5 mol % to 10 mol %, being preferred. If the compound of formula VII' is present at 1.0 equivalent, then $BH_3.Me_2S$ is present at 0.7 to 1.0 equivalent, with 0.7 to 0.8 equivalent, being most preferred. Concentration, extraction, and crystallization leads to the reduced compound of formula VIII'

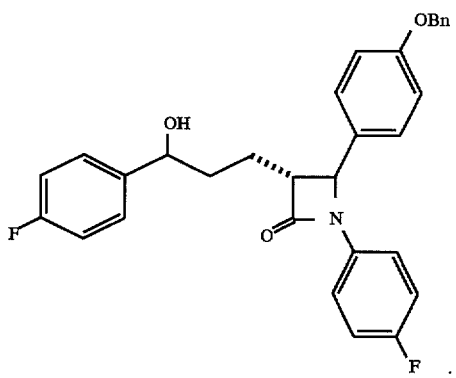

Then the compound of formula VIII' is debenzylated by treatment with a hydrogenating agent such as Pd/C/$HCO_2NH_4$ under a hydrogen atmosphere to obtain a compound of formula I'

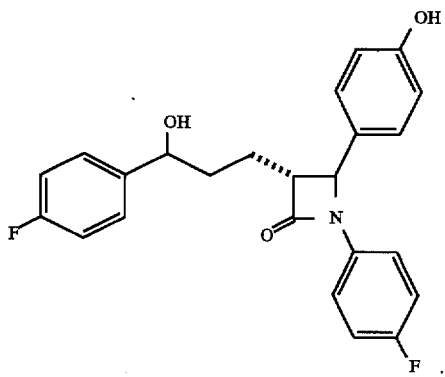

The concentration of Pd/C is 5% to 20% w/w with 10–15% w/w being preferred. The ratio of compound of formula VIII' to Pd/C that is used is 1.0 equivalent of compound of formula VIII', to 2.0 to 5.0 equivalent of Pd/C being used with 3.0 to 4.0 equivalent of Pd/C being preferred. Alternatively, hydrogen gas is used in the ranges from 5 psi(pound per square inch) to 100 psi with 20 to 40 psi being preferred. The solvents which can be employed at this stage of the reaction include methanol, ethanol and i-propanol. As noted above when trans β-lactam is formed, the corresponding cis product is also formed. The cis product is present at this stage of the process in an amount of 5% as compared to the trans product. The cis product may now be purged out by crystallization.

Alternatively, the compound of formula VI' may be made to undergo a double hydrogenation step by reaction under hydrogen in the presence of a hydrogenation catalyst such as palladium on carbon to obtain a compound of formula

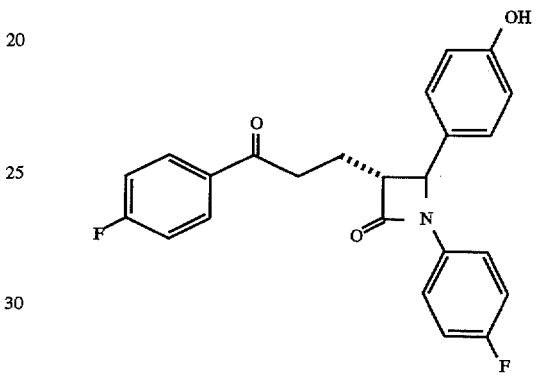

The carbonyl adjacent to the flourobenzene is then chirally reduced to obtain the corresponding compound of formula I' of the invention.

Alternatively, in a process of the invention, a chiral reduction of the —OH in a compound of formula VI' may be conducted to obtain a compound of formula X:

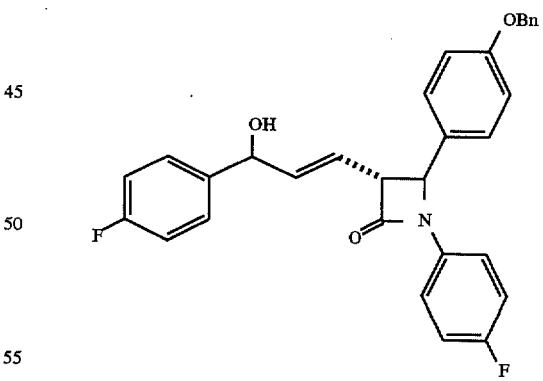

The double bond of this compound of formula X may then be hydrogenated to obtain the compound of formula I'.

In another process of the invention, a compound of formula VI' of the structure:

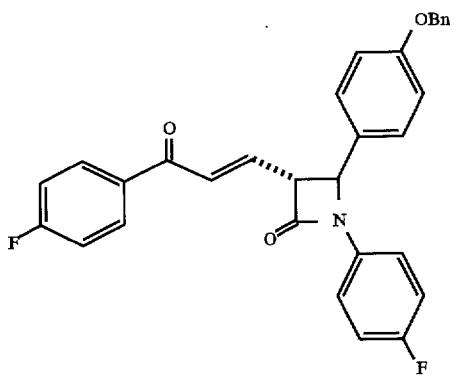

may be converted by the Noyori reduction to the compound of formula I'.

The starting material of the formula

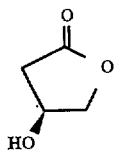

II is known, and may be prepared from s-malic acid of the formula:

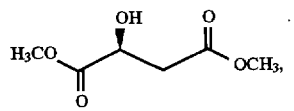

by reduction with BH₃Me₂.S followed by treatment with 5% Na BH₄ to obain a compound of the formula

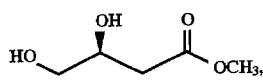

followed by cyclization of this compound with $CF_3CO_2H$ to obtain the γ-lactone of the formula II.

Alternatively, the γ-lactone of the formula II may be obtained from glucose as described in U.S. Pat. 5,292,939, Hollingsworth, which is hereby incorporated by reference.

An imine of formula III'

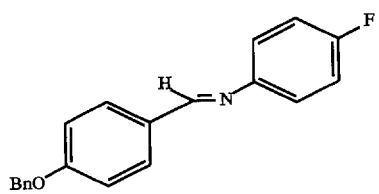

may be prepared by reacting 4-benzyloxy-benzaldehyde with 4-fluoroaniline in a polar organic solvent such as isopropanol at about room temperature. Other imines of the formula III

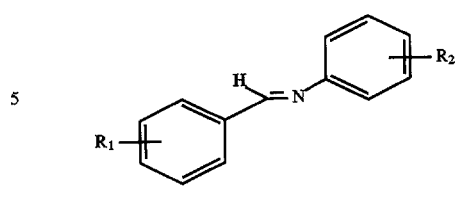

may be prepared in a similar manner, by reacting the appropriate benzaldehyde derivatives and the appropriate aniline derivatives in isopropanol at room temperature for 2 to 3 hours and filtering the reaction mixture to give the product as a solid.

An enolether of the formula E'

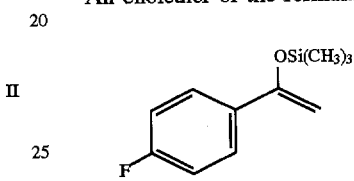

may be prepared by reacting 4-F-acetophenone, (which is a known compound or may be prepared by known methods) in a solution of lithium diisopropylamide in a polar organic solvent such tetrahydrofuran at a temperature in the range of about −30° C. to about −35° C., with quenching by addition of Me₃SiCl, concentration and distillation to obtain the enolether product.

Other enolethers of the formula E

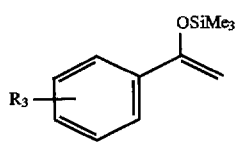

may be prepared in a similar manner.

The following examples illustrate the process of this invention:

EXAMPLE 1

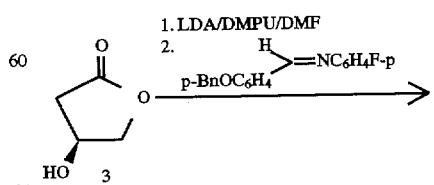

13

-continued

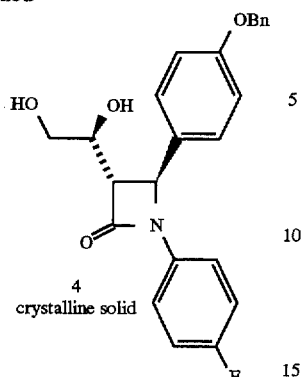

4
crystalline solid

Procedures:

To a 5-liter 3-neck flask equipped with a mechanical stirrer, thermometer, and addition funnel were added 500 mL of THF, 400 mL of 1,3-dimethyl-3,4,5,6-tetrahydropyrimidinone (DMPU), and 120 mL (0.92 mol) of diisopropylamine. To the cooled mixture at –40° to –45° C. was added dropwise 368 mL (0.92 mol) of 2.5M n-BuLi hexane solution. After 20 minutes, 47 g (0.46 mol) of lactone 3 diluted in 250 mL of THF was introduced and the reaction was agitated at –40° to 45° C. for 2 hr. While agitating, dissolve 100 g (0.328 mol) of imine in 1 liter of DMF and then add dropwise through the addition funnel into the reaction mixture at –40° to –45° C. (30 min.). Maintain the reaction at –25° to –30° C. for 14 to 18 hrs and warm to –13° to –17° C. for another 4 hrs as followed by HPLC. Dissolved 14 g of LiCl into 400 mL DMF in a 500 mL flask and added into the reaction mixture. After another 2 hrs at –15° C., 200 mL of HOAc was added to quench the reaction.

The reaction mixture was poured slowly into a 10-liter extractor containing 2 liters of 3N HCl, 1 liter ice, and 2.5 liters of EtOAc. Stir for 15 min. and separated layers. Extract the aqueous layer with 1.0 liter and then with 0.5 liter of EtOAc. Wash the combined organic layer with 4×2 liter brine. Concentration followed by addition with 250 mL toluene to crystallize the trans lactam 4. The solid was filtered and dried at 50° C. to give 85.5 g (64% yield) lactam 4. Mp: 119°–120° C. 1H NMR (CDCl3) 7.38(m,5H), 7.22 (m,4H), 6.90(m,4H), 5.04(d,J=2.0,1H), 5.02(s,2H), 4.21(m, 1H), 3.70(m,1H), 3.6(m,1H), 3.52(d,J=5.0,1H), 3.15(dd,J= 5.2,2.0 Hz), 2.85(t,J=5.3,1H). 13C NMR (CDCl3) 165.5, 160.7, 159.0, 157.5, 136.7, 133.6, 133.5, 129.3, 128.7, 128.2, 127.6, 127.4, 118.8, 118.6, 116.0, 115.5, 70.1, 69.5, 62.9, 56.8.

HRMS: 408.1619(MH+); Calad: 408.1611. [a] –69.78 (c=0.121,THF). Anal. Calad for C24H23FNO4: C,70.75; H,5.44; N, 3.44. Found: C, 70.57; H, 5.56; N, 3.41.

14

EXAMPLE 2

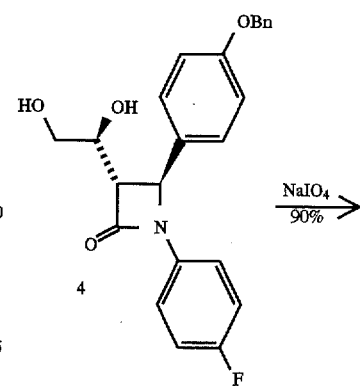

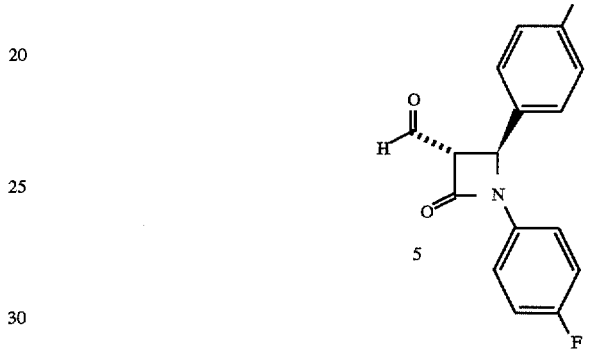

Procedures:

To a 2 liter 3-neck flask equipped with a mechanical stirrer, thermometer, and addition funnel were added sequentially 100 g (0.246 mmol) of lactam 4 and 800 mL of acetonitrile. The mixture was cooled to 10° C. with an ice bath. Dissolve 63 g (0.295 mmol) of NaIO4 in 800 mL of water in a 1 liter flask and transfer it into the addition funnel. Add the NaIO4 solution into the reaction mixture at such a rate to maintain the temperature below 20° C. (20 min.). After addition, allow the reaction to warm to r.t. and stir for 1 to 2 hrs as followed by NMR. Quench the reaction into a 6 liter extractor containing 1.5 liters of ice-brine and 1.5 liters of toluene. Stir and separate layers. Extract the aqueous layer with 500 mL of toluene. Wash the combined organic layer with 2×500 mL brine. Concentrate to about 500 mL for next reaction. MS: 376(MH+), 265, 239. 1H NMR (CDCl3) 9.82(d,J=1.3 Hz,1H), 7.31(m,5H), 7.17(m, 4H), 6.88(m,4H), 5.32(d,J=2.4 Hz,1H), 4.98(s,2H), 4.15(dd, J=2.4,1.3 Hz,1H).

EXAMPLE 3

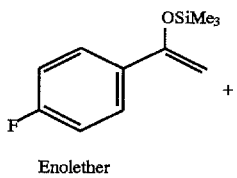

Enolether

+

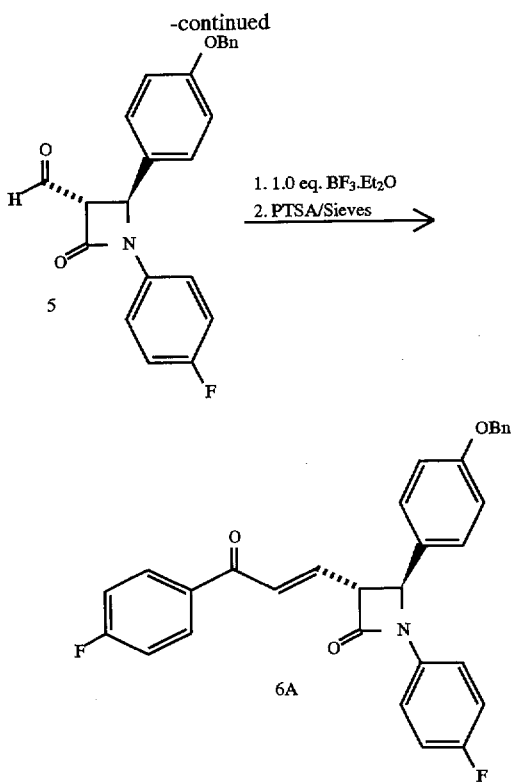

Procedures:

To a 1 liter 3-neck flask equipped with a mechanical stirrer, thermometer, and addition funnel were added at room temperature (r.t.) a 500 mL of toluene solution of 100 g (0.267 mmol) of aldehyde 5 obtained before and 32 mL (0.267 mmol) of $BF_3$.etherate. The mixture was cooled to $-30°$ C. with dry-ice bath. To the cooled mixture was added 56 g (0.267 mmol) of enolether dropwise. The aldol reaction is completed in 5 minutes. To another 5 liter extractor were added 1 liter of saturated $NaHCO_3$ solution, 2 liters of t-BuOMe, and 150 mL of hydrogen peroxide (30%). This quench solution was then cooled to 0° C. with an ice bath. The aldol mixture was added dropwise into the quench solution at 0° C. The quenched mixture was allowed to warm to 15° to 20° C. and the layer was separated. Extract the aqueous layer with 1 liter toluene. Wash the combined organic layer with 2×500 mL and concentrate to about 1 liter for dehydration.

To the 1 liter toluene solution of aldol product obtained above were added 200 g of molecular sieves and 25 g (0.133 mmol) of p-toluenesulfonic acid monohydrate. This mixture was heated to 40° to 50° C. and monitored by NMR (2 to 4 hrs.). The reaction was cooled to 0° C. and filtered through a pad of $MgSO_4$ and then 100 g silica gel. The filtrate was concentrated for next step. Alternatively, the concentrated solution was added to 400 mL of heptane to precipitated the double bond product (99 g, 75% overall yield). MS: 496 (MH+), 359, 305, 238. 1H NMR 8.01(dd,J=8.5,5.5 Hz,1H), 7.40(m,7H), 7.30(m,6H), 7.18(m,2H), 7.22(d,J=8.6,1H), 6.98(t,J=8.5 Hz,1H), 5.08(s,2H), 4.88(d,J=2.4,1H), 4.00(m, 1H).

EXAMPLE 4

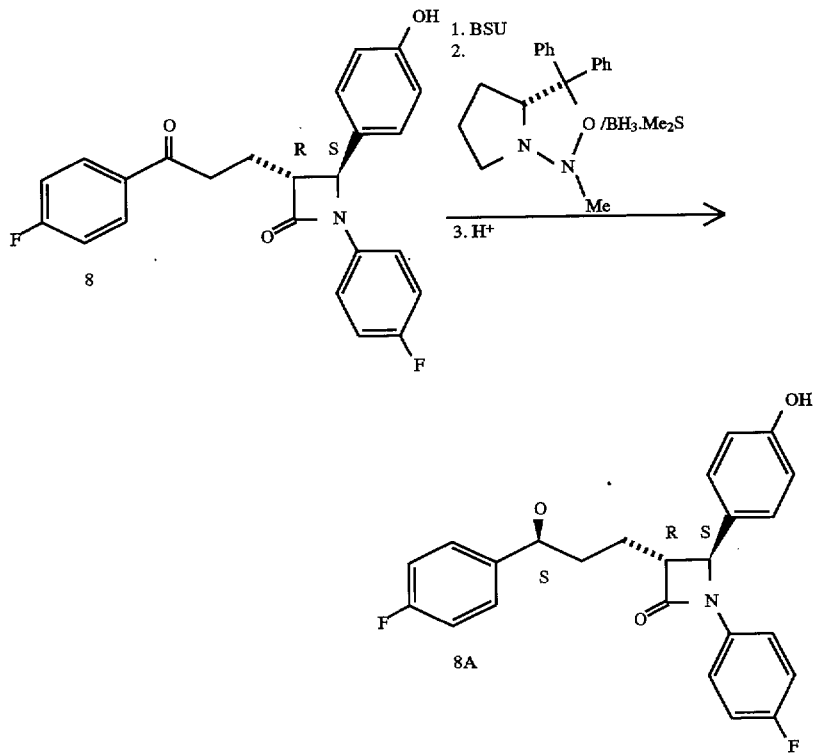

The chiral catalyst was made following the standard procedure: trimethylborxine (28 mg, 0.22 mmol) was added into a solution of dipenylprolinol (75 mg, 0.3 mmol) in toluene (5 ml) and the resultant solution was heated until refluxing. Toluene was distillated and other 5 ml of toluene was added and distillated out. The residue was used directly in the abve reaction.

To a 50 mL oven-dried flask with a magnetic stirrer were added 2.4 g (5.9 mmol) of 8, 10 mL $CH_2Cl_2$, and 0.62 g (3.0 mmol) of bistrimethylsilyl urea (BSU). After 0.5 hr, the reaction was filtered directly into another 50 mL oven-dried flask containing 0.05 eq. of the chiral catalyst at −20° C. To this was added 2.3 mL (4.7 mmol) of 2N $BH_3.Me_2S$. The reaction was stirred at −15° to −20° C. and monitored by TLC and HPLC (3 to 5 hrs). 10 mL methanol/HCl was added followed by concertration. Water and t-BuOMe were added to the residue and extraction with t-BuOMe (×2) to give crude product solution. Concentration of t-BuOMe lead to the recovery of >50% catalyst as the HCl salt after filtration. Crystallization of crude product from Isopropanol/$H_2O$ afford 1.9 g of 8A. 1H NMR(DMSO) 9.54(s,1H), 7.32(dd, J=8.3,5.7 Hz,2H), 7.21(m,4H), 7.35(m,4H), 6.77(d,J=8.3 Hz,2H), 5.3(d,J=4.6 Hz,1H), 4.82(d,J=2.1 Hz,1H), 4.50(m, 1H), 3.10(m,1H), 1,70–1.9(m,4H). 13C NMR(DMSO) 167.4, 162.3, 159.9, 159.3, 157.5, 156.9, 142.3, 142.3, 134.1, 134.0, 128.0, 127.7, 127.6, 118.4, 118.3, 116.0, 115.8, 114.9, 114.7, 71.2, 59.7, 59.5, 36.5, 24.6.

EXAMPLE 5

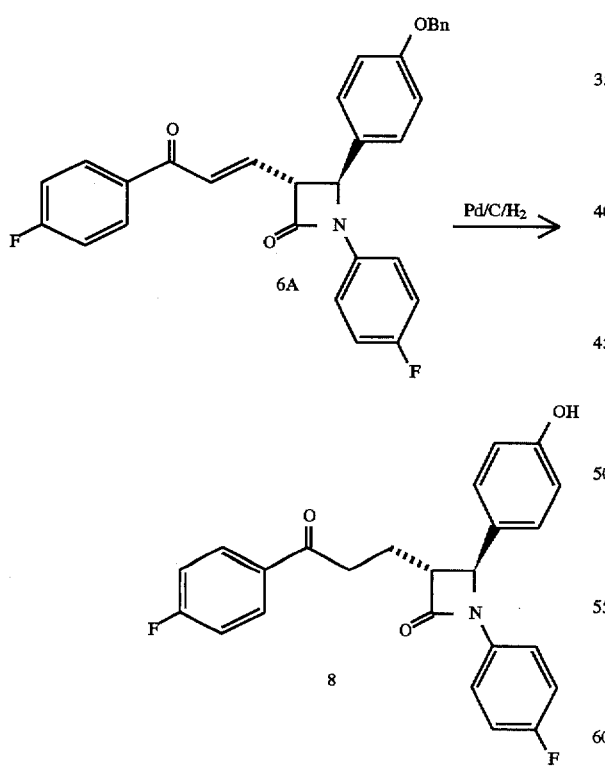

To a 1 liter Parr pressure bottle were added 0.8 g of Palladium on carbon (10%), 1.6 g (19.0 mmol) of $NaHCO_3$, 16 g (32.3 mmol) of 6A in 80 mL of ethyl acetate, and 80 mL of methanol. The bottle was shaken under 30 psi of hydrogen pressure for 2 to 3 hrs as followed by TLC and HPLC. The reaction mixture was filtered through a pad of celite and washed with 200 mL toluene. The filtrate was washed in a 1 liter extractor with 200 mL brine and 2 mL of 3N HCl. After separation of the layers, the organic layer was washed with 2×200 mL brine. Concentration gave 11.8 g (90% yield) product 8. (The reaction also could be carried out as following procedure. A mixture of 1 g 6A in 10 mL of EtOAc, 1 mL of water, and 0.5 (w/w) % of Pd/C (wet) was shaken under 25 psi of $H_2$ for ca. 4 hrs. The mixture was filtered through celite and washed with toluene. Concentration gave product 8, MS: 408(MH+), 297. 1H NMR (CDCl3) 7.95(dd,J=8.6,5.5 Hz,2H), 7.13–7.22(m,4H), 7.09 (t, J=8.6,2H), 6.91(t, J=8.6,2H), 6.80(d, J=8.6 Hz,2H), 4.65 (d, J=2.1,1H), 3.26(m,1H), 2.33(s,1H), 2.25(m,1H). 13C (CDCl3) 197.7, 167.7, 164.5, 160.7, 157.5, 156.3, 133.8, 133.0, 130.9, 130.7, 129.2, 127.5, 118.6, 118.5, 116.2, 116.1, 116.0, 115.8, 115.7, 61.3, 59.7, 35.6, 23.3. Anal. Calcd. for $C_{24}H_{19}NF_2O_3.½H_2O$: C, 69.75; H, 4.47; N, 2.95; F, 9.11. Found: C, 69.23; H, 4.80; N, 3.36; F, 9.13.

EXAMPLE 6

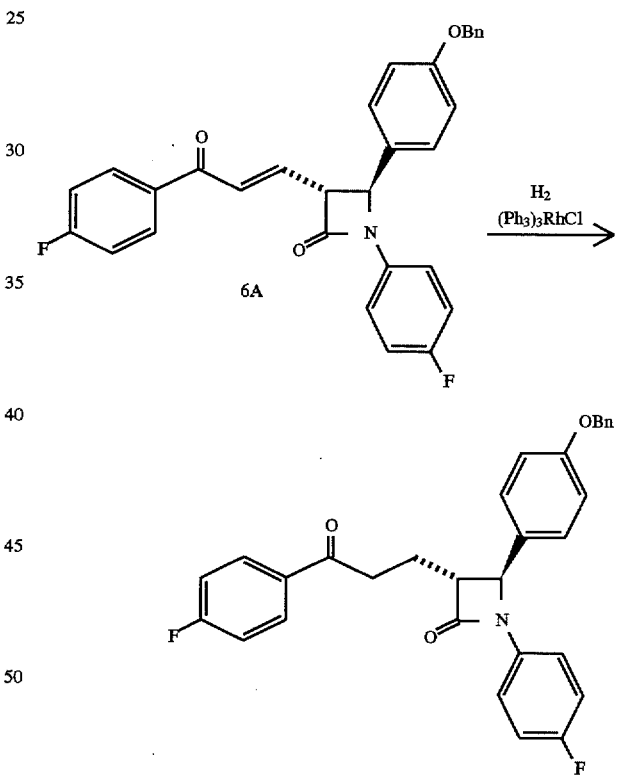

The crude compound 6A, generated from dehydration step from 80 mmol of aldol condensation product, was dissolved in 120 ml of methylene chloride, to which 2.2 g (2.4 mmol) of the catalyst was added. The mixture was subjected hydrogenation at 60 psi for 18 hr. Concentration of the reaction gave a residue of the product, which was separated by column with hexane and EtOAc (90:10) to give 27.5 g pure product, 71% from aldol condensation product as starting material. 1H NMR (CDCl3) 7.98(dd,J=8.5,5.5 Hz,1H), 7.41(m,5H), 7.25(m,4H), 7.12(t,J=8.5,2H), 6.55(m, 4H), 5.04(s,2H), 4.68(d,J=2.1,1H), 3.65(m,1H), 3.28(m, 1H), 3.16(m,1H), 2.40(m,1H), 2.28(m,1H).

We claim:

1. A process for the preparation of a compound of the formula

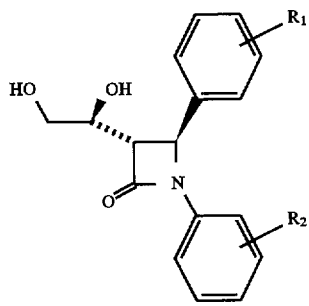

wherein $R_1$ and $R_2$ are independently selected from the group consisting of:

(a) H;
(b) halo;
(c) —$OR_5$, wherein: $R_5$ is selected from the group consisting of H, $C_1$ to $C_6$ alkyl, aryl, aralkyl, heteroaryl, $C_2$ to $C_6$ alkynyl, $C_3$ to $C_7$ cycloalkyl, $C_3$ to $C_7$ cycloalkenyl and —$C(O)R_6$; $R_6$ is selected from the group consisting of $C_1$ to $C_6$ alkyl, aryl and —$OR_7$; and $R_7$ is $C_1$ to $C_6$ alkyl or aryl; and
(d) —$C(O)R_8$, wherein: $R_8$ is selected from the group consisting of $C_1$ to $C_6$ alkyl, aryl, heteroaryl, aralkyl, cycloalkyl, —$OR_9$ and —$N(R_{10})_2$; $R_9$ is selected from the group consisting of $C_1$ to $C_6$ alkyl and aryl; and each $R_{10}$ is independently selected from the group consisting of H, $C_1$ to $C_6$ alkyl and aryl;

comprising reacting a lactone of the formula

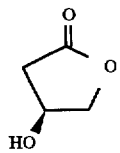

with an imine of the formula

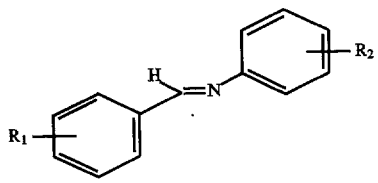

wherein $R_1$ and $R_2$ are as defined above.

2. A process of claim 1 for preparing a compound of the formula

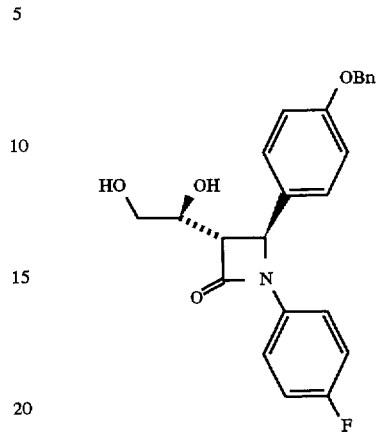

which comprises reacting a compound of the formula

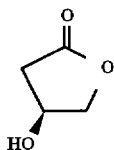

with a compound of the formula

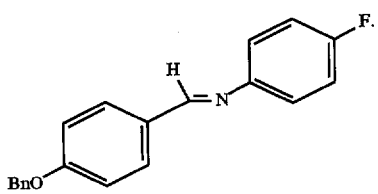

* * * * *